United States Patent [19]
Prince

[11] Patent Number: 4,994,188
[45] Date of Patent: Feb. 19, 1991

[54] ADAPTIVE FILTRATE FLOW CONTROL SYSTEM USING CONTROLLED REDUCTION IN FILTER EFFICIENCY

[75] Inventor: Paul R. Prince, Fountain Valley, Calif.

[73] Assignee: Baxter International Inc., Deerfield, Ill.

[21] Appl. No.: 152,523

[22] Filed: Feb. 5, 1988

[51] Int. Cl.⁵ .............................................. B01D 61/22
[52] U.S. Cl. ................................ 210/636; 210/321.68
[58] Field of Search ........................................ 604/4-7; 210/636, 650, 321.68, 321.87, 782, 784, 321.69; 55/16, 68, 158

[56] References Cited

U.S. PATENT DOCUMENTS

| | | | |
|---|---|---|---|
| 4,579,662 | 4/1986 | Jonsson | 210/636 |
| 4,755,300 | 7/1988 | Fischel et al. | 210/650 |
| 4,806,132 | 2/1989 | Campbell | 55/68 X |

Primary Examiner—Frank Spear
Attorney, Agent, or Firm—Bradford R. L. Price; June M. Bostich

[57] ABSTRACT

The efficiency of a blood plasmapheresis filter is purposefully reduced at low input blood flow rates so as to prevent possibly excessive hematocrit which may make it difficult or impossible to handle the resulting blood cell concentrate (e.g., for infusion purposes) and/or which may cause accompanying red cell damage. Where filter efficiency is a function of rpm of a spinning element, such controlled reduction may be achieved by simply controlling spinner rpm as a function (e.g., linear over at least some range) of the input blood flow rate.

21 Claims, 2 Drawing Sheets

ADAPTIVE FILTRATE FLOW CONTROL SYSTEM USING CONTROLLED REDUCTION IN FILTER EFFICIENCY

BACKGROUND OF THE INVENTION

1. Field of the Invention

This invention relates generally to the control of fluid filtering systems and more particularly to optimum control of fluid filtering systems used to filter blood, blood products or components or other biological fluids such as, for example, in a plasmapheresis system.

2. Related Applications and Prior Art

This invention is related to commonly assigned, allowed U.S. patent application Ser. No. 671,576 filed Nov. 15, 1984 (also published under International Publication No. WO 86/02858), the entire content of which is hereby incorporated by reference. In particular, although the present invention may find utility alone, it is particularly suited as an improvement in the adaptive filter concentrate flow control system and method of this related commonly assigned earlier application.

In this related prior adaptive filter control system, a transmembrane pressure (TMP) operating point is established on an empirically constructed control curve of TMP versus filtrate flow rate so as to automatically maintain substantially maximum filtrate flow rate for any given operating conditions—*without* permitting the TMP to exceed a threshold value at which irreversible filter clogging (and/or hemolysis) begins to occur. For a detailed description of such prior TMP control system, reference should be made to the above cited related publication. However, it will be appreciated that such prior control systems have typically attempted to maximize the efficiency with which the filter operates to perform desirable separation of filtrate from input fluid (while thereby providing a concentrate output as well). For example, in filter systems employing a rotating spinner, the filter efficiency generally increases as the spinner rpm increases and, accordingly, prior control systems have typically operated the spinner at a constant speed chosen to be substantially the highest acceptable speed (e.g., the highest speed that can be used without producing undue hemolysis or other adverse effects).

However, I have now recognized that filter efficiency (i.e., volume of filtrate removed per unit volume of input fluid) can, in some systems, actually become excessive. For example, such filter efficiency is also a function of other parameters (e.g., fluid residence time within the filter) and where some of these other parameters might vary (e.g., as the input blood flow rate and hence residence time does in a typical plasmapheresis system), it is possible that the efficiency of the filtering elements occasionally may be so high that the concentrate output from the filter becomes excessively thick. For example, in a plasmapheresis system, the hematocrit of cell concentrate may become so high that the concentrate becomes sufficiently viscous as to lose some of its fluid-like characteristics and begins to perform somewhat as a soft solid. Since cell concentrates are typically collected from a patient or other donor and periodically reinfused into that donor, this can cause problems in handling the reinfusing process (which, in turn, may cause undue hemolysis of living blood cells included in that concentrate).

In short, in a plasmapheresis system where plasma is separated from whole blood, the separation efficiency of the filter may become so high that the resulting concentrated red cells become excessively concentrated and very difficult to reinfuse into the donor through practical needle sizes in practical times and through practical blood pumps—and may become hemolyzed in the process, another detrimental effect. There may be other fluid filtering and/or processing systems where an input fluid flow rate (or other parameter) might vary so as to sometimes produce such high filtering efficiency that, for some particular applications, it would be preferable to have a lower filtration efficiency. Such problems typically may be encountered more frequently (or be of a more critical nature) where living biological fluids are involved in the filtration process.

In particular, I have now recognized that under low blood flow input rates to a plasmapheresis system, it is possible for filter efficiency to be excessive (e.g., such that the concentrate output from the filter is difficult to handle as a fluid and may become hemolyzed if forced at high flow rates through needles and blood pumps).

SUMMARY OF THE INVENTION

I have now discovered that these problems can be substantially alleviated by purposefully reducing filter efficiency at lower input fluid flow to the filter.

For example, the adaptive filter flow control system of the above referenced related application Ser. No. 671,576 (based upon TMP optimization to provide maximum plasma yield) can continue to be used—while simply inducing lower efficiencies in the filter device for lower input blood flow rates. Lower input blood flow rates may be encountered, for example, where a patient/donor is in poor health and undergoing therapeutic procedures. Inherently poor circulation in the body may well dictate lower blood flow rates input to an attached filtration system. And even some healthy patients forget or refuse to exercise their fist and forearm muscles to increase blood flow rates. As will be appreciated, there are a variety of circumstances where operation at reduced input blood flow rates might be desirable.

Such reduced efficiency inherently removes less plasma at lower blood flow rates and thereby decreases the hematocrit of the concentrate (i.e., as compared to what it would have been using a higher efficiency filtration process). It would seem that a disadvantage of this system would be reduced plasma production rates and resultant longer procedure times. However, with careful selection of efficiency reduction as a function of input blood flow rates, the ultimate result is improved performance in terms of lowered hemolysis, minor reductions in plasma flow rate and lower minimum blood flow rates for satisfactory plasma separation than are available without this feature.

Accordingly, the same filtration system can be used over a wider range of input blood flow conditions without encountering adverse effects such as those mentioned above. In the preferred exemplary embodiment, the fluid filter uses a spinning element and the efficiency of the filtration process is a function of the spinner's rotational speed. In prior systems of this general type (e.g., as sold by the assignee), spinner rpm was maintained at a substantially fixed value (e.g., 3600 rpm). Now, however, the rpm is preferably controlled to be a function (e.g., linear) of input blood flow (e.g., over some predetermined range). At lower input blood flow rates, it may also be desirable to controllably limit the plasma filtrate flow to a maximum value (e.g., which may also be a linear function of input blood flow rate).

BRIEF DESCRIPTION OF THE DRAWINGS

These as well as other objects and advantages of this invention will be better understood and appreciated by carefully studying the following detailed description of a presently preferred exemplary embodiment of this invention when taken in conjunction with the accompanying drawings, of which.

DETAILED DESCRIPTION OF AN EXEMPLARY EMBODIMENT

Figure 1:
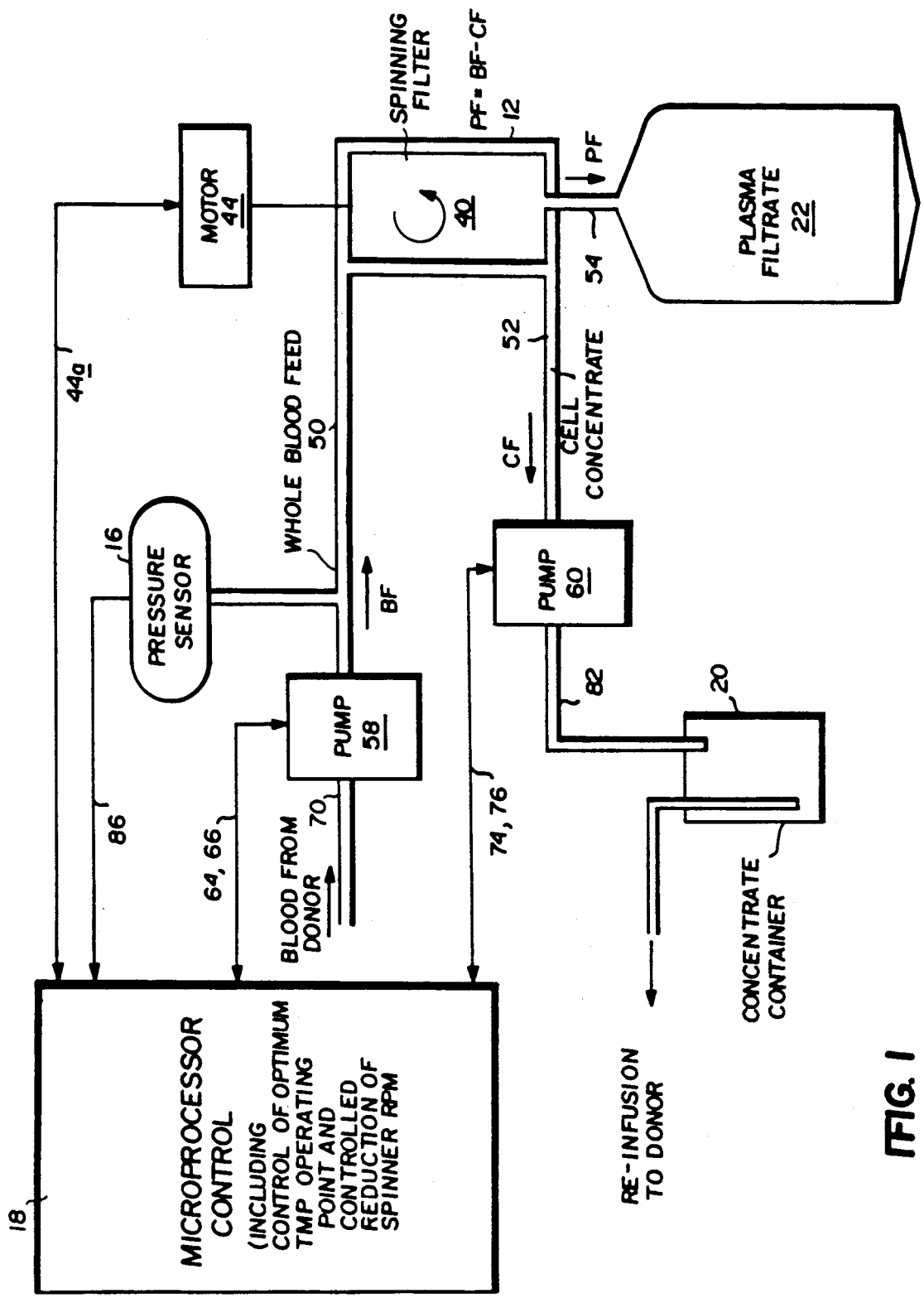
FIG. 1 is a schematic diagram of a portion of an exemplary plasmapheresis system (e.g., of the type described in related U.S. application Ser. No. 671,576) adapted to controllably reduce filter efficiency as a function of input blood flow rate.

The blood plasmapheresis system schematically depicted in FIG. 1 represents a modification of the system described in more detail in the related publication earlier incorporated herein by reference. Similar reference numbers have been used in FIG. 1 so as to facilitate a more detailed understanding of the system by reference to the related publication.

In brief, blood extracted from a donor and subsequently treated with an anti-coagulant is provided via conduit 70 and controlled blood pump 58 to the inlet 50 of a spinning filter system 12 (which includes a spinning filter membrane 40 rotated by motor 44). A plasma filtrate is extracted after passage through the spinning filter membrane via conduit 54 to plasma filtrate collection bag 22 while a cell concentrate residue from the filter system 12 is returned via outlet 52, controlled pump 60 and conduit 82 to a concentrate container 20. Periodically (e.g., upon substantial filling of container 20), the cell concentrate is typically reinfused to the donor. Preferably a single needle system is used where both blood extraction and reinfusion processes time share the same needle (e.g., as in the Autopheresis-C ® device sold by Baxter Healthcare Corporation of Deerfield, Ill.). As will be understood, a plural, needle system may also be used with this invention. And, alternatively, the concentrate may be retained and used for other purposes as will be appreciated.

Pressure sensor 16 is coupled to the inlet of the filter system 12 and is capable of providing an output which represents transmembrane pressure (TMP) via control line 86 to a microprocessor control subsystem 18. Pumps 58 and 60 are typically conventional peristaltic pumps which are controlled by digital speed control signals and which also provide digital position indicating feedback signals via control lines 64, 66 and 74, 76 respectively. Electrical motor 44 is similarly capable of control (and position indicating output) with microprocessor control subsystem 18 via control lines 44a.

As indicated in FIG. 1, the microprocessor control subsystem 18 may include optimized TMP operating point control as explained in more detail in the related publication noted above. In addition, it now includes controlled reduction of spinner rpm so as to controllably reduce the efficiency of the spinning filter system 12 as a function of input blood flow. It will be noted, for example, that the plasma flow (PF) is equal to the input blood flow (BF) less the cell concentrate flow (CF).

Figure 2:
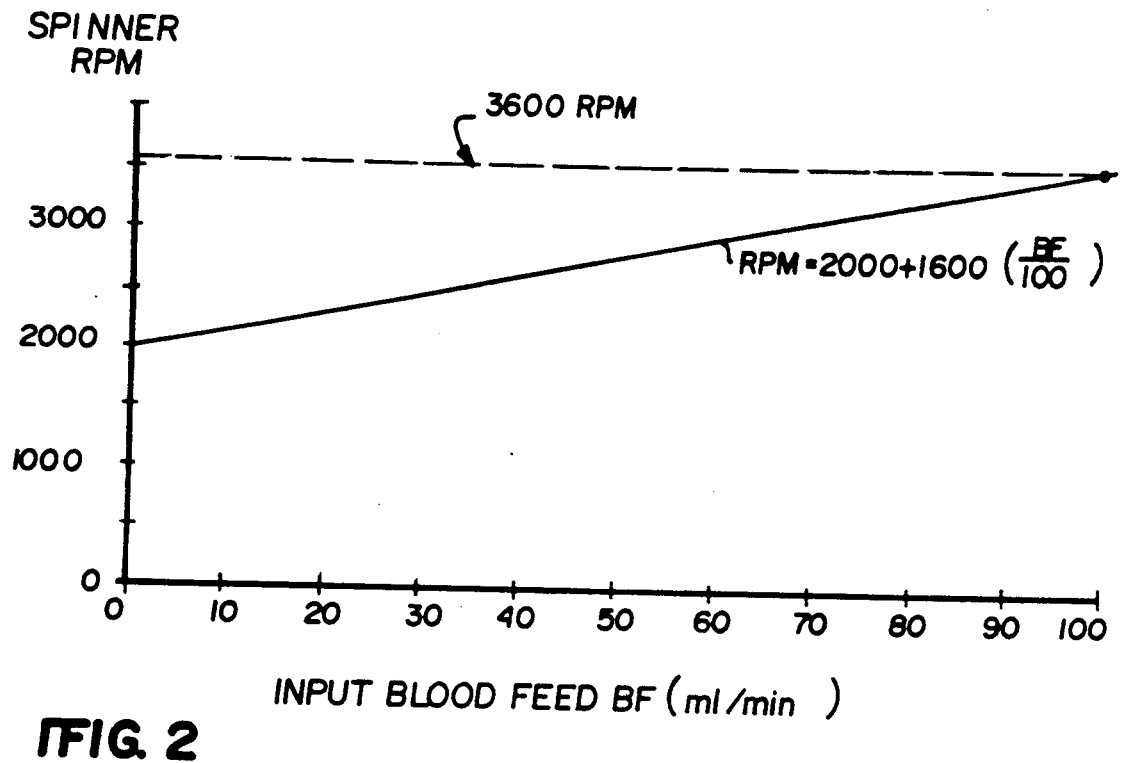
FIG. 2 is a graph showing the manner in which spinner rpm (and hence filter efficiency) is controlled as a function of input blood flow rate.

For example, as depicted graphically in FIG. 2, the rotational speed (e.g., rpm) of motor 44 is now controlled as a linear function of the input blood feed rate BF (e.g., in milliliters per minute) in accordance with the following formula:

$$rpm = 2,000 + 1600\ (BF/100) \qquad [\text{Equation 1}]$$

As will be appreciated, the maximum speed of motor 44 continues to be 3600 rpm as shown by a dashed line in FIG. 2 but may be empirically optimized for various membrane and separation device configurations. In the exemplary embodiment, it is assumed that the blood flow does not exceed 100 milliliters per minute (or that, if it does, the spinner speed could be increased beyond 3600 rpm at higher input flow rates). It should be understood that the maximum spinner rpm and maximum input flow rate parameters are based upon the preferred embodiment but that these values may change with other design changes (e.g., changes in membrane material, radius of the membrane rotor, area of the membrane or gap size, etc). In commercial systems of this type, when the input blood flow falls below a predetermined threshold (e.g., 60 milliliters per minute), sustained plasma separation is impractical and in the Autopheresis-C ® device sold by Baxter Healthcare Corporation, sustained plasma separation is intentionally stopped below this lower limit, or predetermined value. "Predetermined value" is the value below which the machine instructs sustained plasma separation to cease. The reduced spinner rpm and resultant reduced filter efficiency of the exemplary embodiment occur at an input flow rate range immediately above the predetermined value. Such reduced efficiency creates a predetermined value (i.e., for the lower limit of input blood flow rate that will enable satisfactory plasma separation) which is lower than the predetermined value which was heretofore feasible. This may be especially important for therapeutic procedures where a patient-/donor blood circulation system is in poor condition making higher level blood flows undesirable or even impossible.

Measurements indicate that if the rotor speed of the filter in FIG. 1 is reduced from 3600 rpm to zero rpm, the available plasma flow is reduced by a factor of about 50. Accordingly, at low blood flow input rates there are rotor speeds that can be used to reduce the efficiency as desired. Although a linear relationship has been established between input blood flow rate and spinner rpm in the exemplary embodiment, it will be appreciated that other functional relationships can be used as well. Furthermore, although the exemplary embodiment utilizes a particular presently preferred slope for this linear relationship, other linear control curve/slopes could also be implemented.

Figure 3:
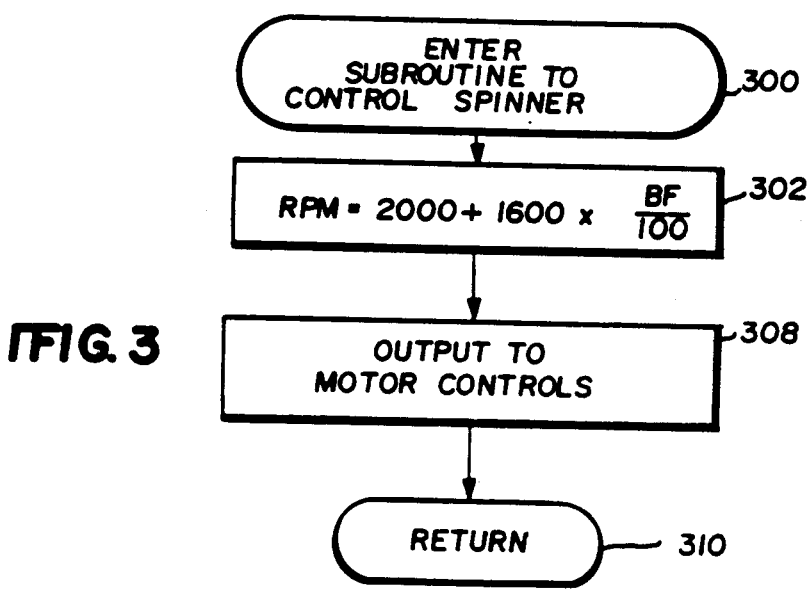
FIG. 3 is a flow diagram of a computer program segment which might be used in the FIG. 1 embodiment for effecting the control depicted in the graph of FIG. 2.

In the exemplary embodiment, other conventional filter control systems continue to be employed as in the past (e.g., TMP operating point optimization, donor vein pressure control subsystems, etc). However, in addition to such conventional controls, a very simple further control can be effected as already described by simply implementing a further computer program subroutine such as that depicted in FIG. 3 (e.g., each time a filter control cycle is performed by the microprocessor 18). Here, upon entry at 300, the new spinner rpm is calculated at 302 in accordance with the functional relationship of FIG. 2 using the current measured or commanded value for blood flow input rate BF.

If a further control below a predetermined threshold is desired, then a test for the threshold may be made and, if appropriate, a status flag may be set and the filtrate flow rate BF is set to be no more than a maximum value (e.g., which also could be a linear function of blood flow input, as well) before the thus derived commands are output to motor controls at 308 and the usual return from the subroutine is taken at 310.

If overshoots or oscillations of TMP are encountered, then it may also be desirable to control the maximum slew rate for increasing plasma flow to be no more than about 1 to 3 milliliters per minute per second.

Although only one exemplary embodiment has been described in detail, those skilled in the art will recognize that many variations and modifications may be made in this exemplary embodiment while still retaining many of the novel features and advantages of this invention. Accordingly, all such variations and modifications are intended to be included within the scope of the appended claims.

What is claimed is:

1. A fluid filtering system comprising:
a fluid filter having controllable rotational speed for separating a filtrate from an input fluid flow and providing a concentrate output fluid flow; and
control means connected to controllably decrease the rotational speed sufficiently to prevent excessive concentration of the concentrate output.

2. A fluid filtering system as in claim 1 wherein said control means controls rotational speed of the spinner element in a linear response to input fluid flow rate over at least a range of input fluid flow rates.

3. A fluid filtering system as in claim 2 where in said control means controls the revolutions-per-minute of the spinner element to approximate 2000 plus 16 times the input fluid flow rate in milliliters per minute.

4. A fluid filtering system as in claim 1, 2 or 3 adapted for plasmapheresis of blood by inclusion of a filter membrane on a spinner suitable for substantially passing blood plasma therethrough while substantially not passing blood cells and wherein the input fluid flow includes blood, the filtrate includes plasma separated from said blood and the concentrate output includes concentrated blood cells having a hematocrit substantially higher than that of the input blood flow and wherein said in response to is controlled in response to input fluid flow.

5. A fluid filtering system as in claim 4 wherein said control means includes TMP control means for maintaining transmembrane pressure across said filter membrane at an optimized operating point where substantially only reversible blood cell blocking of the membrane occurs.

6. A fluid filtering system as in claim 1 or 2 further comprising means for eliminating sustained flow of said filtrate when input fluid flow rate is below a predetermined value.

7. A fluid filtering system as in claim 6 wherein said predetermined value is substantially less than that attainable without reduced filter efficiency.

8. A fluid filtering system as in claim 6 wherein said predetermined value is substantially less than 60 milliliters per minute.

9. In a blood plasmapheresis system of the type which uses a spinning filter element to separate plasma from blood thereby producing blood cell concentrate and which controls operating transmembrane pressure to approximately maximize filtrate plasma flow without irreversible filter clogging, an improvement comprising:
speed control means for controllably changing the rotational speed of the said spinning filter element in response to the input flow rate of blood to prevent excessive hematocrit of said blood cell concentrate.

10. An improved blood plasmapheresis system as in claim 9 wherein the speed control means controls filter element rpm in linear response to blood flow rate input to the filter.

11. An improved plasmapheresis system as in claim 10 wherein said rpm is controlled as a linear function of input blood flow rate over at least a predetermined range of input flow rates.

12. In a blood plasmapheresis system of the type which uses a spinning filter element to separate plasma from blood thereby producing blood cell concentrate and which controls operating transmembrane pressure to approximately maximize filtrate plasma flow without irreversible filter clogging, an improvement comprising:
control means for controllably reducing the speed of said spinning filter element in response to a decrease in the input blood flow rate to prevent excessive hematocrit of said blood cell concentrate.

13. A fluid filtering method comprising:
passing input fluid through a rotating fluid filter having controllable rate of rotation, separating a filtrate flow from said input fluid flow via said filter and providing a concentrate output fluid flow; and
controllably decreasing the rotational rate of the filter sufficiently to prevent excessive concentration of the concentrate output.

14. A fluid filtering method as in claim 13 wherein said controllably decreasing step is performed in response to variations in the input fluid flow rate.

15. A fluid filtering method as in claim 13 wherein said controllably decreasing step includes control of rotational speed of the spinner element as a linear function of input fluid flow rate over at least a range of input fluid flow rates.

16. A fluid filtering method as in claim 15 where in said controllably decreasing step includes control of the revolutions-per-minute of the spinner element to approximate 2000 plus 16 times the input fluid flow rate in millimeters per minute.

17. A fluid filtering method as in claim 13 or 15 further comprising eliminating sustained flow of said filtrate when input fluid flow rate is below a predetermined value.

18. A fluid filtering method as in claim 17 wherein said predetermined value is substantially less than that attainable without reduced filter efficiency.

19. A fluid filtering method as in claim 18 wherein said predetermined value is substantially less than 60 milliliters per minute.

20. A fluid filtering method as in claim 13, 15 or 19, including plasmapheresis of blood by use of a filter membrane on a spinner suitable for substantially passing blood plasma therethrough while substantially not passing blood cells and wherein the input fluid flow includes blood, the filtrate includes plasma separated from said blood and the concentrate output includes concentrated blood cells having a hematocrit substantially higher than that of the input blood flow and wherein said rate of rotation is controlled in response to input fluid flow.

21. A fluid filtering method as in claim 20 including TMP control maintaining transmembrane pressure across said filter membrane at an optimized operating point where substantially only reversible blood cell blocking of the membrane occurs.

* * * * *